United States Patent [19]

Petersson

[11] Patent Number: 5,582,162

[45] Date of Patent: Dec. 10, 1996

[54] INHALER FOR MULTIPLE USE

[75] Inventor: Jan Petersson, Lund, Sweden

[73] Assignee: Astra Aktiebolag, Sodertalje, Sweden

[21] Appl. No.: 436,334

[22] PCT Filed: Nov. 23, 1993

[86] PCT No.: PCT/SE93/01007

§ 371 Date: May 23, 1995

§ 102(e) Date: May 23, 1995

[87] PCT Pub. No.: WO94/12230

PCT Pub. Date: Jun. 9, 1994

[30] Foreign Application Priority Data

Nov. 27, 1992 [SE] Sweden .................. 9203570

[51] Int. Cl.$^6$ .................. A61M 15/00
[52] U.S. Cl. .................. 128/203.15; 128/203.12
[58] Field of Search .................. 128/203.15, 203.12, 128/203.23; 604/58, 59

[56] References Cited

U.S. PATENT DOCUMENTS

| 5,239,991 | 8/1993 | Chawla et al. | 128/203.15 |
| 5,447,151 | 9/1995 | Bruna et al. | 128/203.15 |

FOREIGN PATENT DOCUMENTS

| 55588/90 | 11/1990 | Australia | 604/58 |
| 467172A1 | 1/1992 | European Pat. Off. | |
| 469814A1 | 2/1992 | European Pat. Off. | A61M 15/00 |
| 2667790 | 4/1992 | France | 128/203.15 |
| 2242134A | 9/1991 | United Kingdom | |
| WO90/13327 | 11/1990 | WIPO | A61M 15/00 |
| WO90/13328 | 11/1990 | WIPO | A61M 15/00 |
| 92/00115 | 1/1992 | WIPO | 604/58 |
| 92/04069 | 3/1992 | WIPO | 604/58 |
| WO92/05823 | 4/1992 | WIPO | A61M 15/00 |
| 92005824 | 4/1992 | WIPO | 604/58 |
| WO92/08509 | 5/1992 | WIPO | A61M 15/00 |
| 94/27653 | 12/1994 | WIPO | |

Primary Examiner—Edgar S. Burr
Assistant Examiner—Daniel J. Colilla
Attorney, Agent, or Firm—Fish & Richardson P.C.

[57] ABSTRACT

A multiple dose inhaler for the inhalation of a dry powder medicament is provided. The inhaler includes (a) a housing defining an inlet, an outlet spaced from the inlet, and an airflow path from the inlet to the outlet; (b) an elongate carrier disposed within the housing, a first portion of which carries discrete doses of the medicament, the doses being spaced from one another at predetermined substantially equidistant intervals along the length of the elongate carrier; (c) a dispensing wheel upon which the first portion of the carrier is wound; (d) a take-up wheel constructed to incrementally receive the elongate carrier from the dispensing wheel as it is unwound therefrom during use; (e) an advancement mechanism constructed to incrementally advance the elongate carrier within the housing from the dispensing wheel to the take-up wheel when the inhaler is actuated for use; (f) a brake constructed to releasably resist further advancement of the elongate carrier by the advancement mechanism after the elongate carrier has advanced an incremental distance substantially equal to the predetermined distance between the discrete doses; and (g) a trigger constructed to engage and release the brake, allowing further advancement of the elongate carrier.

24 Claims, 5 Drawing Sheets

INHALER FOR MULTIPLE USE

TECHNICAL FIELD OF THE INVENTION

The present invention relates to an inhaler for multiple use for a medicament in powdered form to be used in conjunction with an elongate carrier carrying discrete doses of said medicament, said elongated carrier comprising a carrier body and a peelable cover strip covering and enclosing said discrete doses, said inhaler comprising a housing, an air inlet, a powder dispensing station and an air outlet, said inlet, said outlet and said dispensing station being interconnected by an air conduit for inhaling, said inhaler further comprising displacing means for moving said elongate carrier so as to successively locate a discrete dose in said dispensing station and means for separating said peelable cover strip from said carrier body in connection with said dispensing station.

BACKGROUND TO THE INVENTION

An inhaler of the above general kind has several advantages in comparison to standard multiple powder inhalers containing a large number of doses in a store for the powdered drug from which the powder is fed to a dispensing station.

The drug thus can be protected against moisture in a simple and efficient way since each individual dose of the drug can be tightly enclosed and sealed between the cover strip and the elongate carrier. The utilization of the drug is high since there is no store that may have to be overfilled to ensure definitely that there is drug available as long as the dose counter indicates there should be. The number of doses can be varied in a simple way by cutting different lengths from a continuous elongate carrier. It is easy to arrange a simple counting device indicating the number of doses used or remaining. A simple indication that all doses have been used up may be obtained merely by the fact that the carrier is used up, which is easy to determine. The device may finally also be designed to be reusable several times which would make the device cheap in use, since it is easy for the patient to refill the device in a safe way without any risk of exposing the drug to moisture.

A further advantage of using an elongate carrier is that the counting device may be dispensed with entirely if each dose is numbered, i.e. a numeral is assigned to each dose, the numerals being consecutively visible through an opening in the housing. Preferably the doses are numbered backwards with the highest numeral assigned to the first dose. In this way a simple way of indicating the number of doses remaining may be obtained without any need for a counting mechanism.

An inhaler of the kind as described in the introduction above and in the preamble of the main claim is for instance disclosed in GB-A-2 242 134. This prior art device utilizes the depressions or cavities in an elongated carrier in cooperation with indexing or registering means in order to control that the depressions containing the doses are positioned correctly in the dispensing station. In one embodiment the device is provided with a spool taking up the cover strip (the indexing means are here engaging the depressions which are used to move the carrier). However, since the diameter of the spool taking up the cover strip will vary in dependence of the amount of strip wound on the spool, the winding speed of the cover strip consequently also will vary, whereas the movement of the carrier will not. To compensate for this, the spool taking up the cover strip has been provided with a rather complicated friction coupling allowing the take-up spool to slip in relation to the movement of the elongated carrier.

In an alternative embodiment which is suggested, but not described in detail, the distances between the depressions in the elongate carrier have been varied in order to compensate for the above effect, which however complicates the manufacturing and filling process for the elongate carrier. Further, the number of doses generally cannot easily be varied by cutting a long prefabricated carrier part into pieces having different lengths.

In both cases the elongate carrier (and the depressions in particular) must be comparatively stiff to permit the use of the depressions as actuating means in conjunction with indexing or registering means. This may be undesirable in some applications. The use of the depressions in combination with the indexing means also results in limitations on the size of the depressions since the depressions, apart from the stiffness mentioned above, also have to have a minimum size in order not to slip through the indexing or registering means. This means that the doses also have to have a minimum size.

Some other related prior art devices are disclosed in for instance WO 90/13327, WO 90/13328, and EP-A1-0 469 814.

BRIEF DESCRIPTION OF THE INVENTIVE CONCEPT

The object of the invention is to obtain an inhaler of the kind described introductorily which also allows the use of carriers having small cavities or depressions containing small doses of highly potent drugs and which, if necessary, may be made of a material which is sufficiently flexible to be deformed to some extent in the dispensing station in order to facilitate the ejection of the powdered drug from the depression before or during inhalation. A further object of the invention is to provide an inhaler for multiple doses which has a simple construction and which is cheap to produce.

In one aspect, the invention features a multiple dose inhaler for a medicament in powdered form. The inhaler includes: (a) a housing defining an inlet, an outlet spaced from the inlet, and an airflow path from the inlet to the outlet; (b) an elongate carrier disposed within the housing, a first portion of which carries discrete doses of the medicament, the doses being spaced from one another at predetermined substantially equidistant intervals along the length Of the elongate carrier; (c) a dispensing wheel upon which the first portion of the elongated carrier is wound; (d) a take-up wheel constructed to incrementally receive the elongate carrier from the dispensing wheel as it is unwound therefrom during use; (e) an advancement mechanism constructed to incrementally advance the elongate carrier within the housing from the dispensing wheel to the take-up wheel when the inhaler is actuated for use; (f) a brake constructed to releasably resist further advancement of the elongate carrier by the advancement mechanism after the elongate carrier has advanced an incremental distance substantially equal to the predetermined distance between the discrete doses; and (g) a trigger constructed to engage and release the brake, allowing further advancement of the elongate carrier.

SHORT DESCRIPTION OF THE APPENDED DRAWINGS

FIG. 1 is a schematic drawing of a preferred embodiment showing the basic principles of the inhaler, FIGS. 2–5 are schematic drawings that show the ratchet and pawl/cam follower advancement mechanism shown in FIG. 1 in a sequence of positions, starting at a first position, in which the pawl is engaged and the cam follower is not (FIG. 2), changing position in FIGS. 3 and 4, and returning to the starting position in FIG. 5.

DETAILED DESCRIPTION OF A PREFERRED EMBODIMENT OF THE INVENTION

It should be noted that all terms used below relating to the exact orientation in the appended drawings, such as "upper", "lower", "clockwise" etc only relate to the drawings as such and are not to be construed as limiting the scope of the invention.

Figure 1:
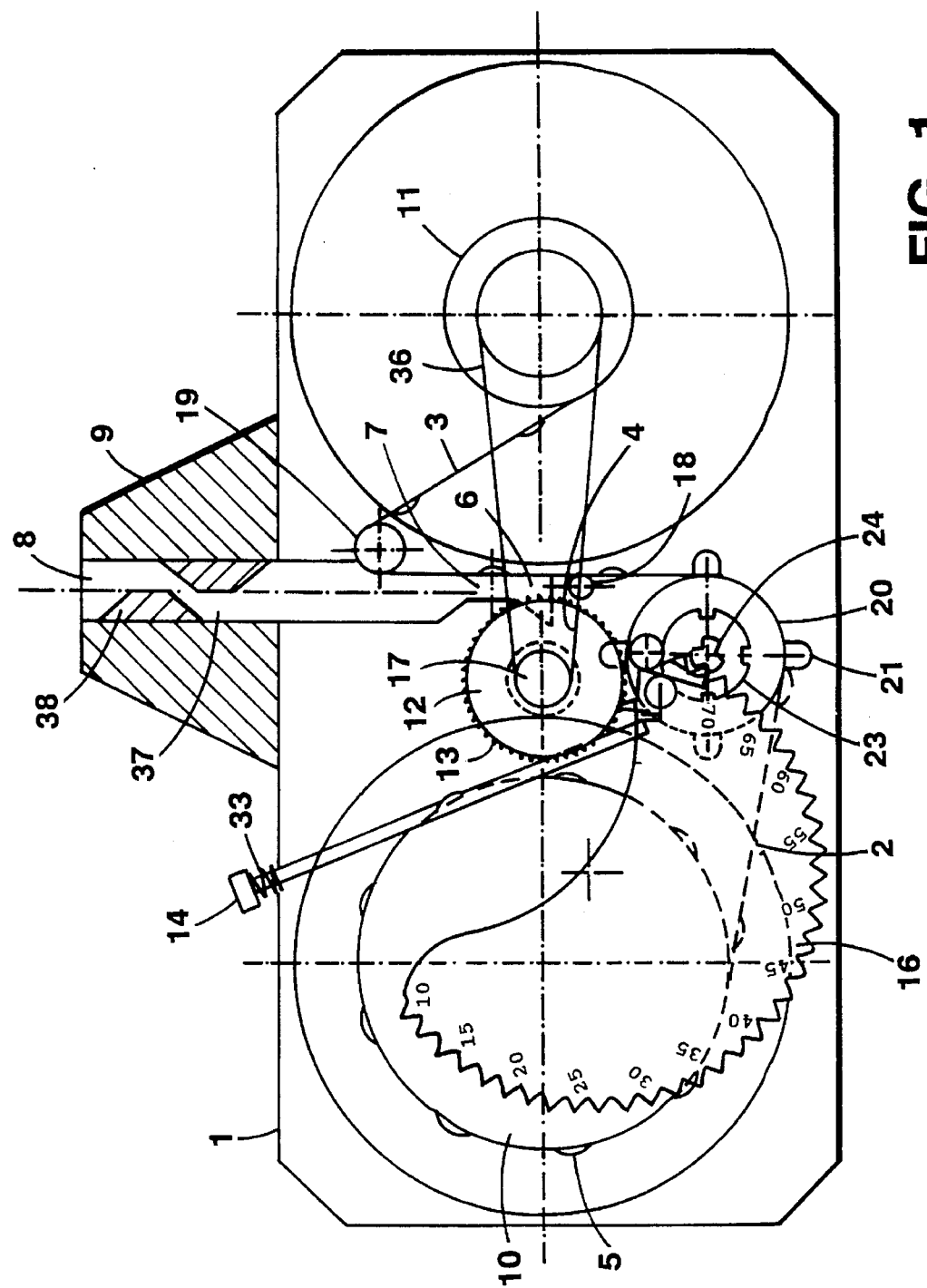

As can be seen in FIG. 1, the inhaler in a preferred embodiment comprises a housing 1 with a mouth-piece 9. An air inlet 6 is connected to an air outlet 8 via a dispensing station 7 by means of an air conduit 37. An elongated carrier 2 carrying the doses of the drug comprises a lower tape 3 provided with depressions or cavities 5 containing the drug and a continuous peelable cover strip 4 sealing the cavities. The peelable strip 4 is separated from the lower tape 3 at the dispensing station 7, thus exposing the drug in any cavity located in the dispensing station. The dispensing station 7 is formed as a constriction in the air conduit 37, the lower tape 3 forming one of the walls of the constriction. When the inhaler is actuated for use, a cavity 5 is located centrally in the dispensing station 7.

The cover strip 4 is guided away from the lower tape 3 by means of a guide roller 18 located just before the dispensing station 7 and is wound onto a first take-up spool 15 fixedly attached to an actuating wheel 12 partly extending outside the housing 1. The spool 15 and the actuating wheel are rotatably supported on a common axis 17 supported in the housing 1. The periphery of the actuating wheel 12 is provided with teeth 13, which may serve a double function, namely to enhance the grip when the wheel is actuated manually (in an embodiment in which the periphey of the wheel extends outside the housing) and to cooperate with a double pawl 22 in a manner to be described more in detail below in connection with FIGS. 2–5.

The lower tape 3 is guided onto a second take-up spool 11 by means of a second guide roller 19 located after the dispensing station 7. The second take-up spool 11 is driven by the first take-up spool 15 by means of a belt 36 which for instance may be made of rubber. This belt will serve as a cheap and simple friction coupling compensating for any differences in the respective winding speeds of the lower tape 3 and the cover strip 4. Normally there should not be any great differences in the winding speeds provided that the thickness of the lower tape and the thickness of the cover strip are more or less equal and that the two take-up spools have the same diameter and provided that any influence from the cavities in the carrier can be disregarded.

The two guide rollers 18, 19 also serve to orient and align the lower tape 3 correctly in the dispensing station 7. Since the dispensing station 7 is designed as a constriction in the air conduit 37, the air respired through the air conduit will move rapidly and turbulently across the mouth of the cavity in the lower tape, thus lifting the dose of powdered drug out from the cavity.

The airstream will move the powdered dose up along the air conduit 37 to the mouth-piece 9. The air conduit 37 and/or the mouth-piece 9 is provided with deaggregation means 38 to break up any aggregates that could have been created in the powder formed dose. Upon impaction the medicament with powder aggregates will break up into a finely divided medicament having a high amount of particles having a size within the respiratory range, that is smaller than 10 µm, preferably smaller than 5 µm.

The construction form and size of the deaggregation means can be varied but preferably they can have a form of deflector devices as described in EP-B-237 507, or comprise planar impaction surfaces as described in WO 92/04069 or any other suitable form which provides a deaggregating effect. The deaggregation means could be provided in the air conduit 37 and/or in the mouthpiece 9 as shown in FIG. 1.

If a fresh tape is to be mounted in the inhaler, the free end of the cover strip 4 is firmly attached to the take-up spool 15 and the free end of the lower tape 3 is attached to the take-up spool 11.

The carrier 2 is stored on and unwound from a third spool 10 which may be replaceable.

The carrier 2 further is provided with equidistant perforations (not shown) which preferably are located along the longitudinal edges of the carrier. These perforations are intended to engage sprockets 21 on a sprocket wheel 20 which is rotatably journaled in the housing 1 such that the sprocket wheel 20 rotates with the carrier 2 when the carrier 2 is displaced longitudinally. A ratchet wheel 23 provided with recesses 25 and a cog wheel 24 provided with recesses 26 further are attached coaxially and rigidly with the sprocket wheel 20 so as to co-rotate therewith. The cog wheel 24 serves to actuate a counting device in the shape of a cog wheel 16 provided with a scale visible through an aperture in the housing (not shown) and serves additionally as a cam for a purpose which will be described more in detail below.

FIGS. 2–5 illustrate the functional details of the indexing means and particularly some details not shown in FIG. 1.

These drawings thus show the carrier 2 with the lower tape 3, the depressions 5 and the cover strip 4, the sprocket wheel 20 with the sprockets 21, the ratchet wheel 23, the cog wheel 24, the guide roller 18, the double pawl 22, the actuating wheel 12 with the teeth 13 and the take-up spool 15, and the trigger 14.

The drawings further show how the double pawl 22 is provided with a first pawl 27 cooperating with the ratchet wheel 23 and a second pawl 28 cooperating with the teeth 13 of the actuating wheel 12. The first and the second pawl are fixedly attached relative to each other. The double pawl 22 is carried swingably on an axle 30 and is provided with a eccentric shoulder 29 cooperating with the trigger 14.

The indexing means further is provided with a detent 32 cooperating with a shoulder 34 on the second pawl 28. The shoulder 34 has an upper and a lower surface for engagement with the detent 32. The upper surface is oriented generally in parallel with the longitudinal extent of the detent 32. The lower surface, however, is oriented generally perpendicularly to the upper surface.

A cam follower 31 cooperating with the cog wheel 24 is fixedly attached relative to the detent 32. The detent and the follower are rotatably carried on an axle 35. The detent and follower are spring-biased in a counter-clockwise direction whereas the double pawl is spring-biased in a clockwise direction. The trigger 14 is spring-loaded by a spring 33 biasing the trigger outwardly from the housing 1.

Figure 2:
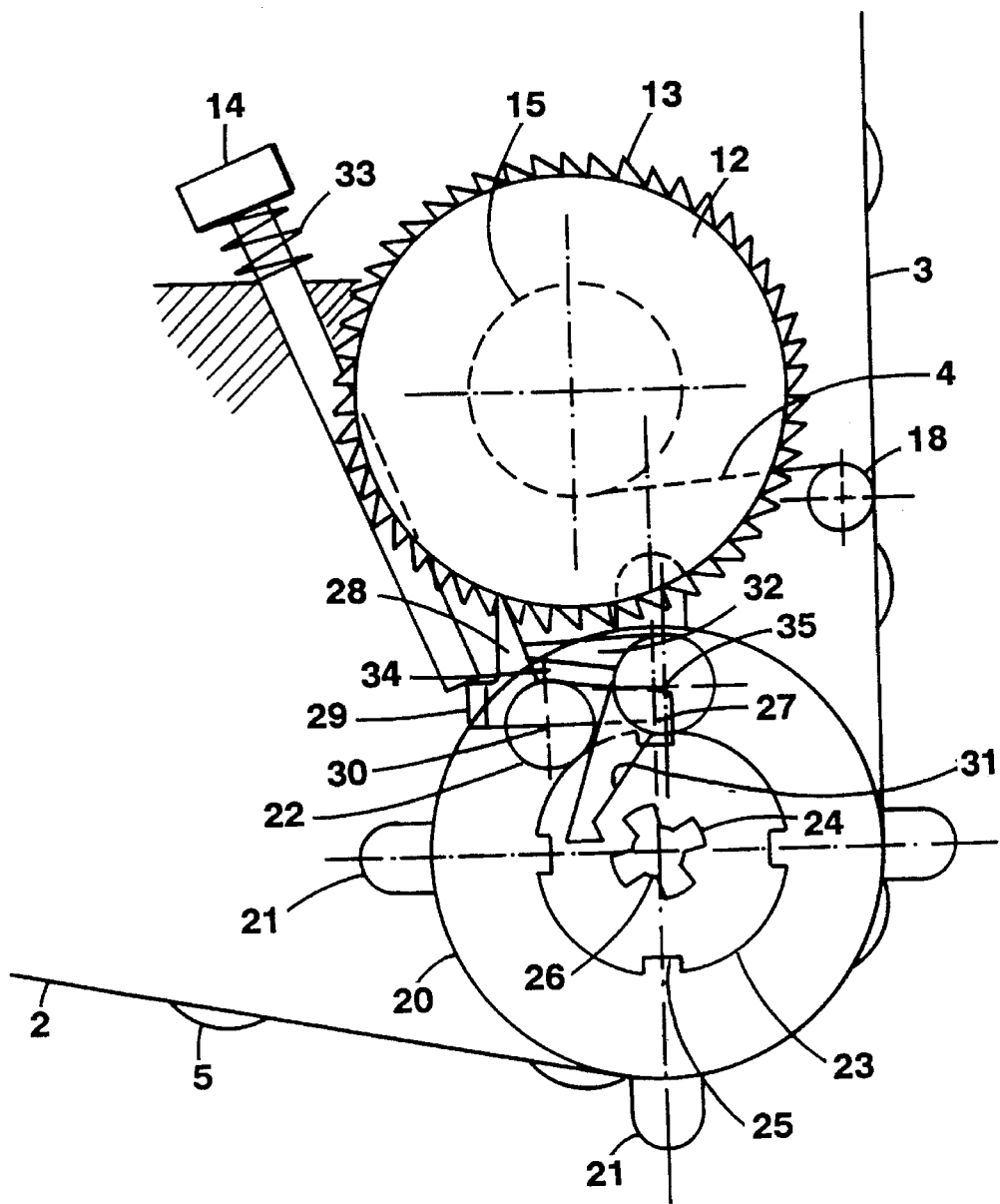

FIG. 2 illustrates the initial position of the indexing means, before a cavity containing a new dose is moved into the dispensing station. In this position the trigger 14 rests on the shoulder 29. The pawl 28 is in engagement with the teeth 13 by which means the actuating wheel 12 is blocked. The pawl 27 is further in engagement with the ratchet wheel 23 by which means the sprocket wheel 20 is blocked. Consequently the carrier 2 is blocked. The detent 32 finally rests upon the upper surface of the shoulder 34, thus keeping the cam follower out of engagement with the cog wheel or cam 24.

Figure 3:
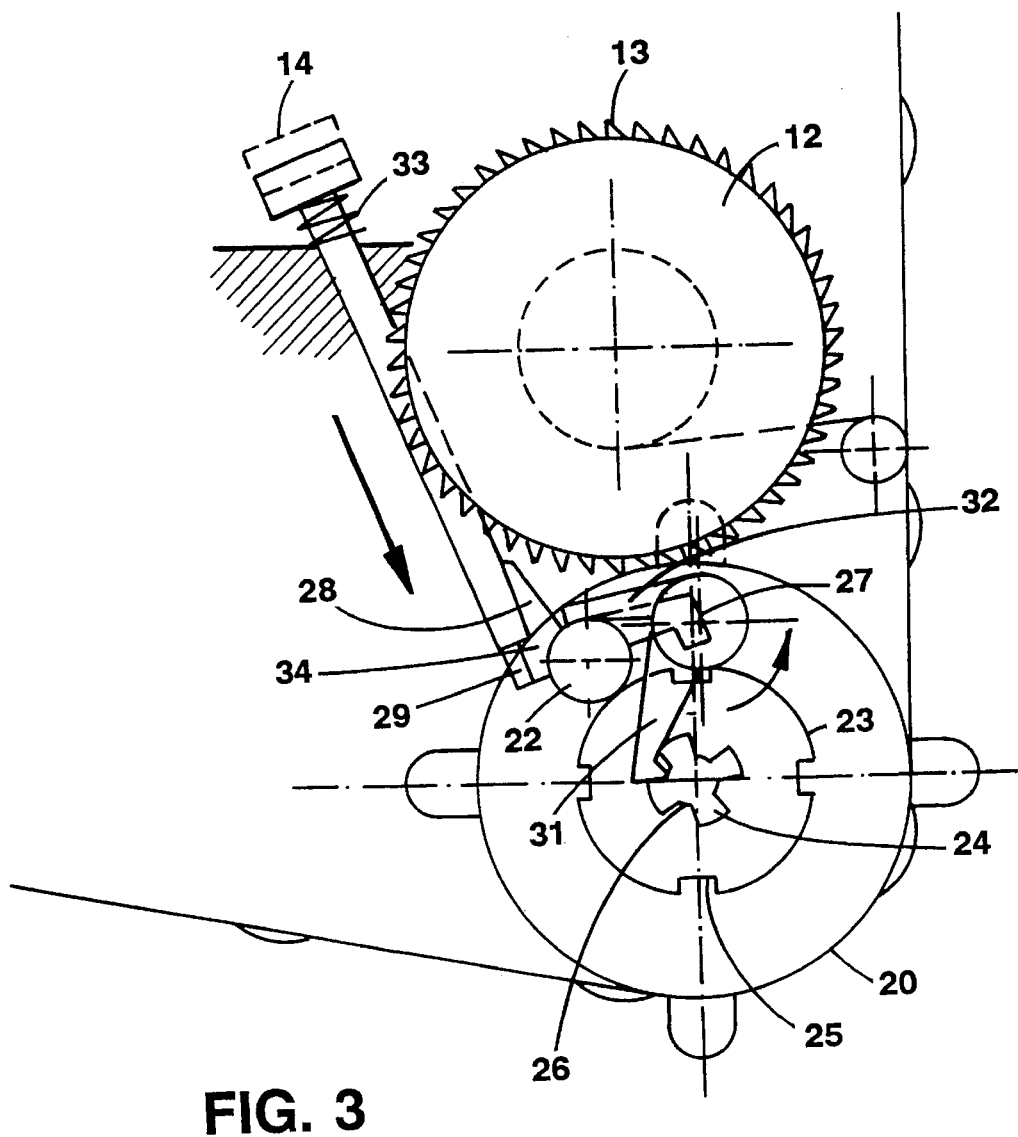

When the inhaler is to be used, a cavity containing a new dose of the powdered drug normally is moved into the dispensing station. In order to free the wheels 12 and 20 and to allow this movement of the carrier, the trigger 14 is depressed against the action of the spring 33 as shown in FIG. 3. The trigger acts on and displaces the shoulder 29 causing the double pawl 22 to swing counter-clockwise against the spring bias. By this means the second pawl 28 is disengaged from the teeth 13 of the actuating wheel 12 and the first pawl 27 is disengaged from the recesses 25 on the ratchet wheel 23. The detent 32 slides off the upper surface of the shoulder 34 under the influence of the spring bias and swings slightly counterclockwise such that its end rests against the lower surface of the shoulder 34, thus preventing the double pawl 22 from swinging clockwise, thereby keeping both pawls 27 and 28 disengaged from their respective wheels. As a result of the above movement of the detent 32, the cam follower 31 will swing into one of the recesses 26 of the cog or cam wheel 24.

It should be noted that the recesses 26 on the wheel 24 are oriented such relative to the recesses 25 on the ratchet wheel 23 that the cam follower 31 can swing into a recess 26 when the pawl 27 can engage a recess 25. Both the actuating wheel 12 and the sprocket wheel 20 now are free to rotate.

Figure 4:
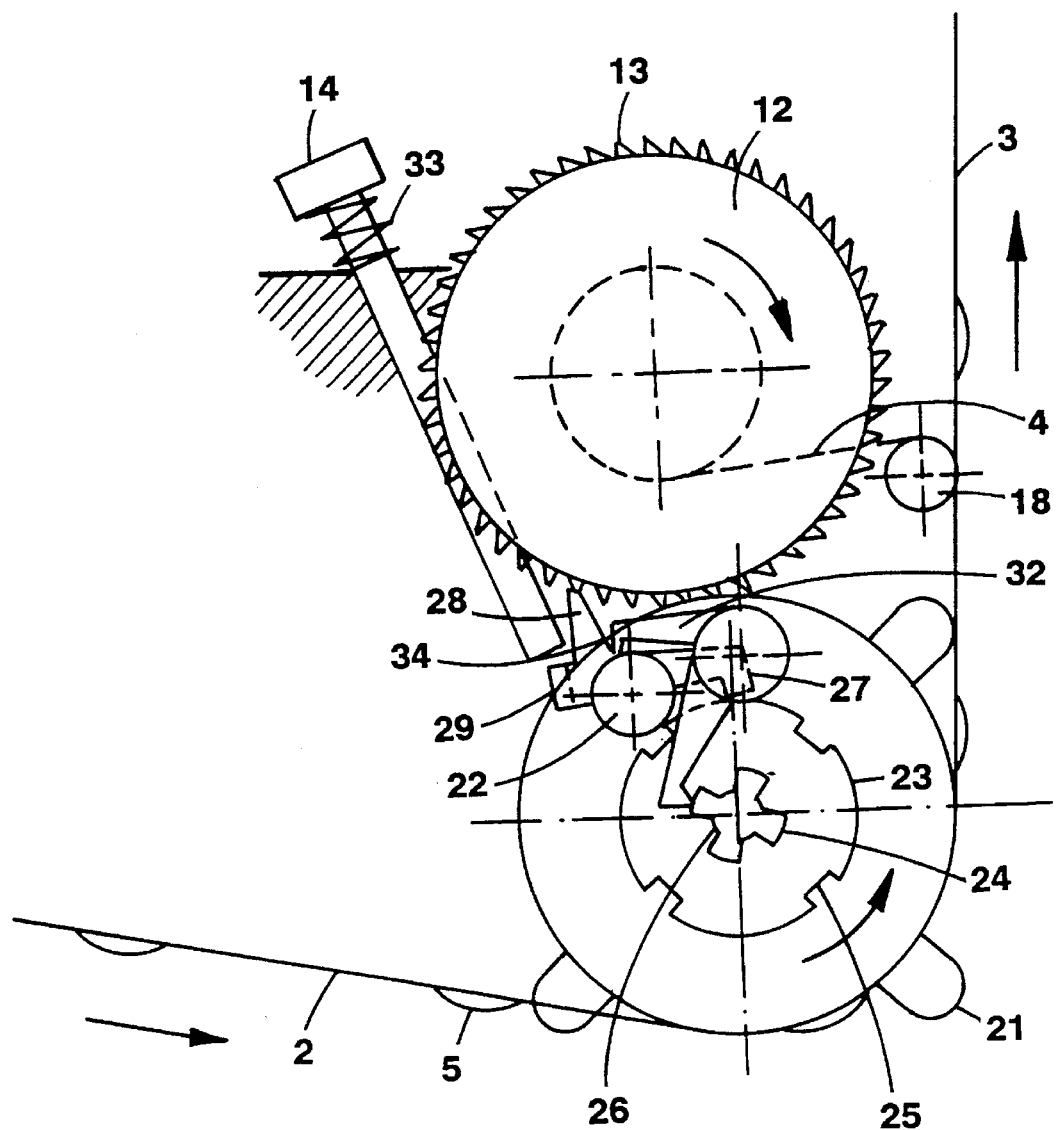

FIG. 4 illustrates what happens when the actuating wheel is rotated in order to move a new dose of the drug into the dispensing station.

Since the cover strip 4 is firmly attached to the spool 15, a rotation of the actuating wheel 12 will result in that the cover strip is wound onto the spool 15, thus pulling the carrier 2 and the lower tape 3 forward through the inhaler. This forward movement is however only possible as long as the sprocket wheel 20 and the take-up spool 15 remain free to rotate. The lower tape 3 will be wound onto the spool 11 since the spool 11 is driven by the actuating wheel 12 via the spool 15 and the belt 36.

The cam follower 31 will swing clockwise under the influence of the teeth on the cog wheel 24 which in this instance serve as cams. This will force the detent 32 out of engagement with the lower surface of the shoulder 34 to slide on to the upper surface of the shoulder, thus freeing the double pawl 22. When the detent 32 rests on the upper surface of the shoulder 34, the cam follower 31 will return to its original position, out of engagement with the cog or cam wheel 24.

The double pawl 22 can however not swing back and block the respective wheels 12 and 23 since the pawl 27 now slides upon the outer periphery of the ratchet wheel between two adjacent recesses 25. The actuating wheel thus can be rotated until the pawl 27 engages the next recess 25 on the periphery of the ratchet wheel 23.

Figure 5:
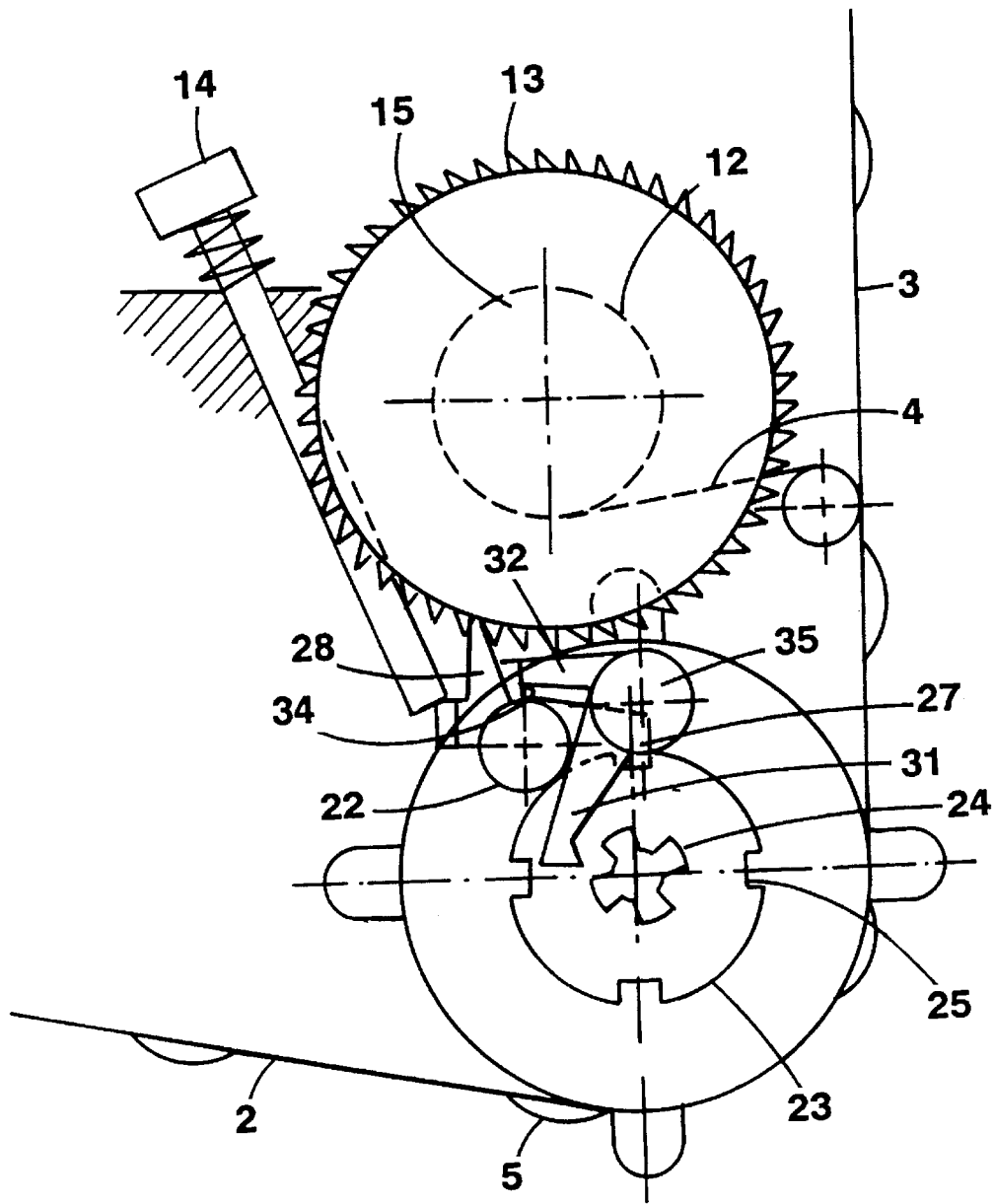

When the pawl 27 again engages a recess 25 on the ratchet wheel 23, the component parts of the indexing means have returned to its original state before the actuation of the trigger, as can be seen in FIG. 5.

The angular distance between the recesses 25 is chosen such that this rotation of the ratchet wheel 23 corresponds to an angular movement of the sprocket wheel 20 corresponding exactly to the distance between two adjacent depressions or cavities. In this way it is ensured that a cavity containing a fresh, exposed dose of the powdered drug replaces the cavity previously being located in the dispensing station, irrespective of whether the dose contained in that cavity has been used or not (if a dose has been left exposed in the dispensing station for some time, a new dose preferably should be used), and the inhaler is ready for inhalation.

A clear indication that all doses of drug are used up and that the inhaler is empty is obtained by the fact that the actuating wheel will rotate freely as soon as the end of the carrier 2 has left the sprocket wheel 20. This is due to the fact that the sprocket wheel 20 together with the ratchet wheel 23 will not rotate with the actuating wheel when the carrier has left the sprocket wheel. This results in that the indexing means will remain in the state shown in FIG. 3 after the depression of the trigger 14, in which state the actuating wheel is freely rotatable, since the cam follower 35 will not disengage the detent 32 from the lower surface of the shoulder 34 and the pawl 28 will remain disengaged from the actuating wheel.

Since the cover strip 4 is used to pull the carrier 2 through the inhaler and the lower tape 3 serves no other purpose than to form sealable containers or cavities for each individual dose of the drug, the design of, the dimensions of and the choice of materials in the lower tape 3 and the cavities can be varied so as to optimize the release of the powdered drug from the cavities into the air stream.

The cavities thus for instance may be designed to be relatively shallow which may facilitate the release of the drug. The thickness or the material of the tape can be chosen such that the walls, particularly the bottom in the cavities is flexible enough to allow the cavities to be deformed or flexed as a consequence of the subpressure obtained at the mouths of the cavities when the accelerated airstream in the constriction sweeps past the mouths. This flexing may aid in breaking up the powder in the cavities, thus facilitating the release of the powder into the airstream. The movement of the bottom may even be strong enough to literally eject the powder from the cavities.

It would also be possible to deform the cavities mechanically by placing the lower tape under tension over an even surface or shoulder in the area of the constriction, the surface pushing the bottom of the cavities upwardly in the dispensing station when the tape is pulled over the surface. By these means the powder would be more or less pushed into the airstream.

POSSIBLE MODIFICATIONS OF THE INHALER

The inhaler of course can be modified in many ways within the scope of the attached claims.

Thus the indexing means in the embodiment illustrated comprise a sprocket wheel for engagement with perforations in the tape. This sprocket wheel is illustrated as being located before the place of separation of the lower tape and the cover strip. The sprocket wheel may however be located after the place of separation and after the dispensing station, engaging the lower tape only or the cover strip only. This may for instance have advantages in regard of the design of the inhaler. However, in some embodiments the carrier might have to be relatively strong in order not to be deformed against the sprocket wheel under the influence of the pulling action when the sprocket wheel is blocked after a forward movement of the carrier, since such deformation may result in a incorrect positioning of a cavity in the dispensing station. Depending on the respective materials used, it may normally be preferable to locate the sprocket wheel before the place of separation as illustrated in the preferred embodiment, in this way utilizing the combined strength of the lower tape and the cover strip.

In this context it should however be noted that the carrier does not risk being deformed in the preferred embodiment illustrated above, since the sprocket wheel 20 and the take-up spool 15 for the cover strip 4 are locked simultaneously at the end of an intermittent movement of the carrier.

However, if the sprocket wheel is not locked at the end of each intermittent movement, it may be advisable to provide a friction brake or an equivalent thereof acting on the sprocket wheel or on the carrier before the dispensing station in order to counteract any forces transmitted from the take-up spool to the elongate carrier, thus preventing the carrier to move after the end of the intermittent movement under the action of these forces, in order to ensure that the cavity always is located correctly in the dispensing station.

It is of course not necessary that indexing wheel, as for instance the sprocket wheel, is locked at the end of each movement of the carrier. It would in principle be sufficient if the indexing wheel merely activated the mechanism for locking the take-up spool in a distinct and secure manner.

It may also be possible to use a friction roller or wheel, which for instance may be knurled, engaging the carrier as an indexing means. This roller should cooperate with a second roller also preferably having a frictional surface, the carrier being held between the two rollers. Depending on the circumstances, one or both of the two rollers may be locked after a predetermined angle of rotation in order to aid in blocking the movement of the carrier when a new or fresh dose of the medicament has been introduced into the dispensing station.

The elongate carrier may also be mounted on a storage roll in an exchangeable cassette, the free end of the carrier being attached to a take up spool, also located in the cassette.

I claim:

1. A multiple dose inhaler for a medicament in powdered form comprising:
   (a) a housing defining an inlet, an outlet spaced from said inlet, and an airflow path from said inlet to said outlet;
   (b) an elongate carrier disposed within said housing, a first portion of which carries discrete doses of the medicament, said doses being spaced from one another at predetermined substantially equidistant intervals along the length of said elongate carrier;
   (c) a dispensing wheel upon which said first portion of said elongated carrier is wound;
   (d) a take-up wheel constructed to incrementally receive said elongate carrier from said dispensing wheel as it is unwound therefrom during use;
   (e) an advancement mechanism constructed to incrementally advance said elongate carrier within said housing from said dispensing wheel to said take-up wheel when said inhaler is actuated for use;
   (f) a brake constructed to releasably resist further advancement of said elongate carrier by said advancement mechanism after said elongate carrier has advanced an incremental distance substantially equal to said predetermined distance between said discrete doses; and
   (g) a trigger constructed to engage and release said brake, allowing further advancement of said elongate carrier.

2. An inhaler of claim 1 wherein said brake comprises an indexing wheel constructed to engage regions of said elongated carrier, and a member constructed to engage said indexing wheel to resist rotation of said indexing wheel after a predetermined angle of rotation.

3. An inhaler of claim 2 wherein said elongated carrier includes a plurality of perforations and said indexing wheel includes a plurality of sprockets constructed to engage said perforations.

4. An inhaler of claim 1 wherein said elongate carrier includes a plurality of equidistant depressions and each of said discrete doses is contained by a said equidistant depression.

5. An inhaler of claim 1 further comprising a cover sheet disposed over said elongated carrier to protect said discrete doses.

6. An inhaler of claim 5 further comprising a second take-up spool to receive said cover sheet as it is removed from said elongated carrier to allow delivery of said discrete doses.

7. An inhaler of claim 6 wherein said second take-up spool is driven, causing said cover sheet to be peeled from said elongated carrier by the rotation of said second take-up spool.

8. An inhaler of claim 7 wherein said advancement mechanism comprises an actuating wheel constructed to drive said take-up spool for said elongated carrier, and said second take-up spool is mounted rigidly and coaxially on said actuating wheel for rotation therewith.

9. An inhaler of claim 1 further comprising a mouth-piece mounted at said air outlet, said mouth-piece defining an opening through which said doses can be inhaled during use.

10. An inhaler of claim 1 further comprising a deaggregation portion provided in said airflow path.

11. An inhaler of claim 10 further comprising a deaggregation portion provided in said mouthpiece.

12. A multiple dose inhaler for a medicament in powdered form comprising:
   (a) a housing defining an inlet, an outlet spaced from said inlet, and an airflow path from said inlet to said outlet; and, within said housing,
   (b) an elongate carrier, a first portion of which carries discrete doses of the medicament, said doses being spaced from one another at predetermined substantially equidistant intervals along the length of said elongate carrier;
   (c) a dispensing wheel upon which said first portion of said elongated carrier is wound;
   (d) a take-up wheel constructed to incrementally receive said elongate carrier from said dispensing wheel as it is unwound therefrom during use;
   (e) an advancement mechanism constructed to incrementally advance said elongate carrier within said housing from said dispensing wheel to said take-up wheel when said inhaler is actuated for use, said advancement mechanism comprising a ratcheted wheel having a plurality of teeth;
   (f) a brake constructed to releasably resist further advancement of said elongate carrier by said advancement mechanism after said elongate carrier has advanced an incremental distance substantially equal to said predetermined distance between said discrete doses, said brake comprising a first pawl rotatably mounted for movement between a first position in which said first pawl engages said teeth of said ratcheted wheel and a second position in which said first pawl is free of said teeth; and (g) a trigger constructed to release said brake by engaging said first pawl and rotating it to said second position, allowing further advancement of said elongate carrier.

13. An inhaler of claim 12 wherein said take-up wheel is driven by said actuating wheel.

14. An inhaler of claim 13 wherein said brake further comprises a sprocket wheel constructed to engage said elongated carrier as said elongated carrier is advanced between said dispensing wheel and said take-up wheel.

15. An inhaler of claim 14 wherein said brake further comprises an inner cog wheel and an outer ratchet wheel, mounted rigidly and coaxially on said sprocket wheel, a second pawl constructed to rotate with said first pawl between a first position in which said second pawl engages said outer ratchet wheel and a second position in which it is disengaged therefrom, said second pawl being in said first and second positions when said first pawl is in said first and second positions, respectively.

16. An inhaler of claim 15 wherein said cog wheel is constructed to drive a counting disc carrying a consecutive series of indicia, and an opening in said housing through which at least one of said indicia can be viewed, causing said counting disc to be intermittently rotated synchronously with each intermittent movement of said elongate carrier.

17. An inhaler of claim 15 wherein said first and second pawls are biased toward their respective first positions.

18. An inhaler of claim 17 wherein said brake further comprises a cam follower rotatably mounted for movement between a first position in which a first portion of said cam follower engages a first surface of said first pawl when said first pawl is in its second position, preventing movement of said first pawl toward its first position, and a second position in which said first portion of said cam follower engages a second surface of said first pawl, preventing rotation of said cam follower.

19. An inhaler of claim 18 wherein said cam follower is biased towards its first position.

20. An inhaler of claim 19 wherein said cam follower further comprises a second portion constructed to engage said ratchet wheel when said cam follower is in its first position and to slide out of engagement and over a peripheral surface of said ratchet wheel when said cam follower is rotated towards its second position.

21. An inhaler of claim 14 wherein said elongated carrier includes a plurality of perforations and said sprocket wheel includes a plurality of sprockets positioned for engagement with said perforations.

22. An inhaler of claim 12 wherein said elongate carrier includes a plurality of equidistant depressions and each of said discrete doses is contained by a said equidistant depression.

23. An inhaler of claim 12 further comprising a cover sheet disposed over said elongated carrier to protect said discrete doses.

24. A method of delivering a finely divided powdered medicament to a human comprising the steps of:

(a) providing an inhaler comprising:
  (i) a housing defining an inlet, an outlet spaced from said inlet, and an airflow path from said inlet to said outlet;
  (ii) an elongate carrier disposed within said housing, a first portion of which carries discrete doses of the medicament, said doses being spaced from one another at predetermined substantially equidistant intervals along the length of said elongate carrier;
  (iii) a dispensing wheel upon which said first portion of said elongated carrier is wound;
  (iv) a take-up wheel constructed to incrementally receive said elongate carrier from said dispensing wheel as it is unwound therefrom during use;
  (v) an advancement mechanism constructed to incrementally advance said elongate carrier within said housing from said dispensing wheel to said take-up wheel when said inhaler is actuated for use;
  (vi) a brake constructed to releasably resist further advancement of said elongate carrier by said advancement mechanism after said elongate carrier has advanced an incremental distance substantially equal to said predetermined distance between said discrete doses; and
  (vii) a trigger constructed to engage and release said brake, allowing further advancement of said elongate carrier;

(b) causing the human to actuate said advancement mechanism to move a said dose into said airflow path; and (c) causing the human to inhale through said outlet to receive said dose through said outlet.

* * * * *

UNITED STATES PATENT AND TRADEMARK OFFICE
CERTIFICATE OF CORRECTION

PATENT NO. : 5,582,162
DATED : December 10, 1996
INVENTOR(S) : Jan Petersson

It is certified that error appears in the above-identified patent and that said Letters Patent is hereby corrected as shown below:

<u>Title page,</u>
Item [56] add -- FOREIGN PATENT DOCUMENTS -- -- 95/11715  5/1995  WIPO --.

Signed and Sealed this

Twenty-eighth Day of May, 2002

*Attest:*

*Attesting Officer*

JAMES E. ROGAN
*Director of the United States Patent and Trademark Office*